United States Patent [19]

Ferrante

[11] Patent Number: 5,380,332
[45] Date of Patent: Jan. 10, 1995

[54] SYSTEM AND METHOD FOR PROFILING AN ANATOMIC PATELLA

[75] Inventor: Joseph M. Ferrante, Cordova, Tenn.

[73] Assignee: Wright Medical Technology, Inc., Arlington, Tenn.

[21] Appl. No.: 166,157

[22] Filed: Dec. 10, 1993

Related U.S. Application Data

[63] Continuation of Ser. No. 976,615, Nov. 16, 1992, abandoned.

[51] Int. Cl.6 .......................... A61B 17/00; A61F 2/32
[52] U.S. Cl. ...................................... 606/79; 606/85; 606/86; 606/88
[58] Field of Search .......... 606/79, 80, 82, 83, 606/86, 87, 88; 51/204 R, 205 WG, 206 R, 207, 208, 209 R, 210

[56] References Cited

U.S. PATENT DOCUMENTS

| | | | |
|---|---|---|---|
| 1,294,423 | 2/1919 | Davis | 51/206 R |
| 2,344,880 | 3/1944 | Johnson | 51/205 WG |
| 2,455,655 | 12/1948 | Carroll | 606/82 |
| 3,125,088 | 3/1964 | O'Neal | 51/206 R |
| 4,004,581 | 1/1977 | Heimke | 606/82 |
| 4,059,115 | 11/1977 | Jumashev | 606/82 |
| 4,069,824 | 1/1978 | Weinstock | 606/82 |
| 4,142,517 | 3/1979 | Stavropoulos | 606/79 |
| 4,708,133 | 11/1987 | Comparetto | 606/82 |
| 4,955,888 | 9/1990 | Slocum | 606/82 |
| 5,035,698 | 7/1991 | Comparetto | 606/79 |

*Primary Examiner*—Michael A. Brown
*Attorney, Agent, or Firm*—Walker, McKenzie & Walker

[57] ABSTRACT

A system for profiling an anatomic patella includes a grinding tool having a handle portion and a grinding surface operatively connected thereto. The grinding surface is a concave dome shape for forming a dome shaped surface on an anatomic patella. A guide member is connectable to the patella. The guide member guides the grinding surface of the guide tool to a predetermined medial portion of the patella to shape the patella to match an articulating surface of a femoral prosthesis.

5 Claims, 1 Drawing Sheet

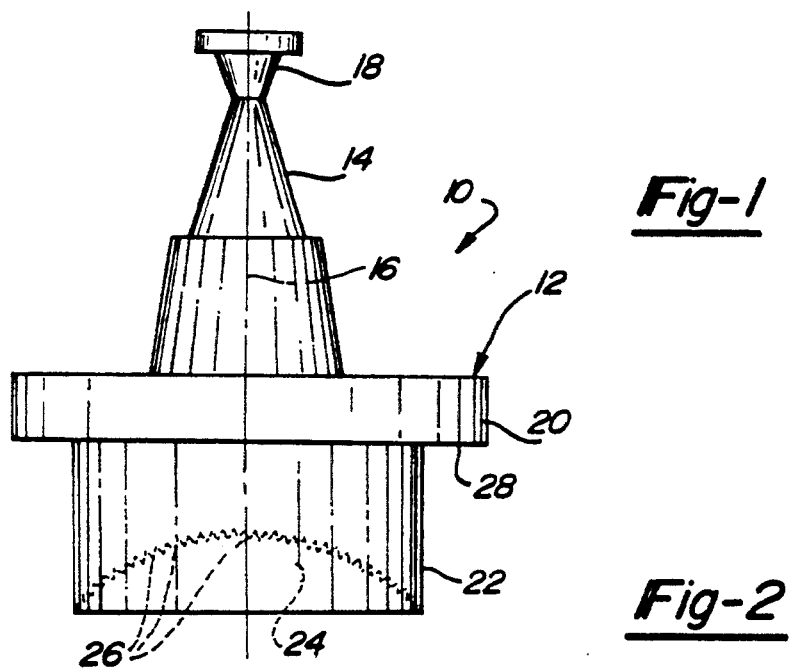
Fig-1
Fig-2
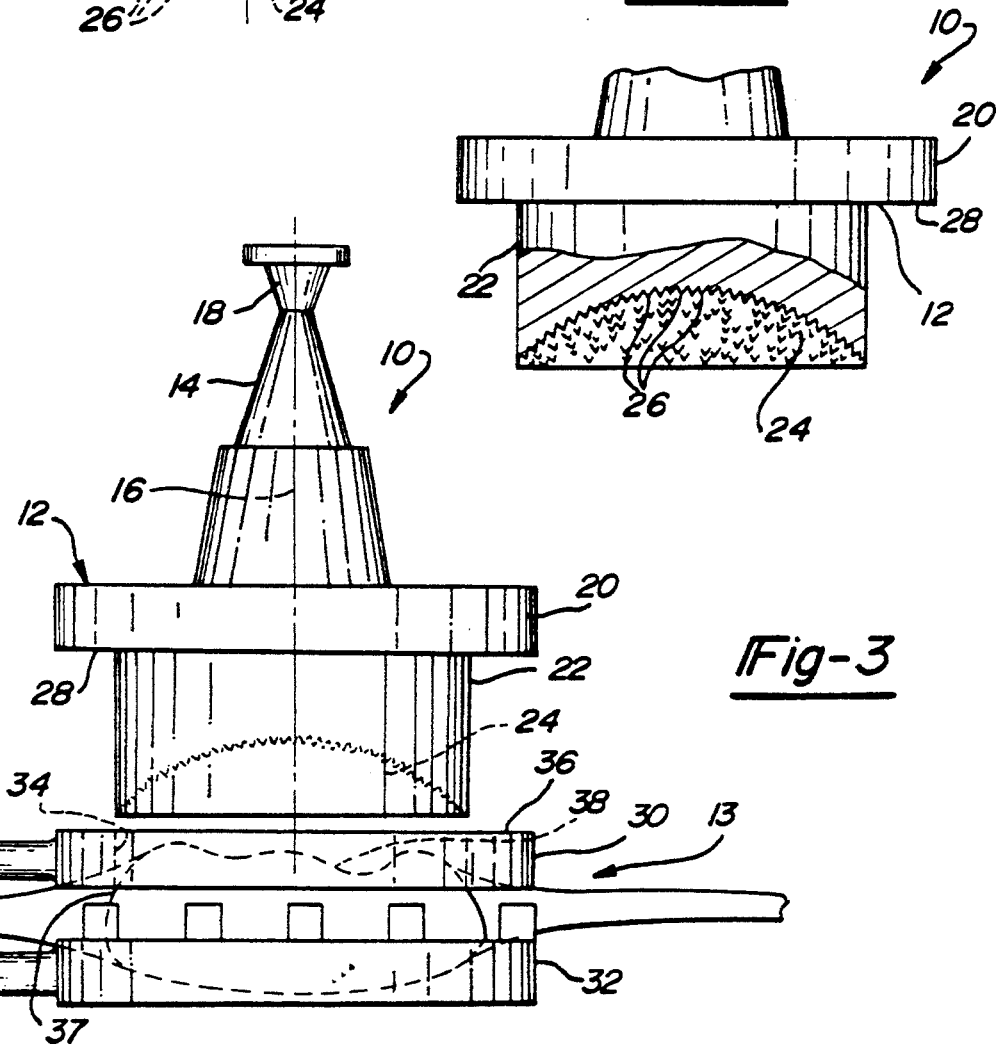
Fig-3

SYSTEM AND METHOD FOR PROFILING AN ANATOMIC PATELLA

This application is a continuation of application, application Ser. No. 07/976,615, filed Nov. 16, 1992, now abandoned.

TECHNICAL FIELD

The present invention relates generally to methods and apparatus for knee arthroplasty. More specifically, the present invention relates to preparing an anatomic patella during arthroplasty of the knee joint.

BACKGROUND OF THE INVENTION

Total knee arthroplasty involves preparing the bone of a distal femur and proximal tibia each to receive an implant prosthetic component. Presently accepted practice prefers maintenance of the natural patella as opposed to patella replacement.

It has been proven clinically that the anatomical patella, when not resurfaced, forms a soft tissue layer which distorts patellar tracking against the trochlear groove of a femoral prosthesis. Interoperatively, a practitioner retracts the patella and removes bone from the posterior of the patella resulting in a rounded shape. This reshaping of the anatomical patella allows it to move along the patellar track of the femoral component. However, this visual method of patellar bone removal usually leaves an uneven posterior surface and can results in subluxation of the patella.

The prior art is deficient in providing method and apparatus for profiling an anatomic patella to positively track the femoral component and thereby help to maintain positive ligament balance.

SUMMARY OF THE INVENTION

According to the present invention, a system for profiling an anatomic patella is provided comprising a tool including a handle portion and a grinding surface operatively connected to the handle. The grinding surface defines a concave domed shape for forming a corresponding, or complementary, domed surface to a posterior surface of the anatomic patella. Guide means is provided for connecting the tool in mating engagement with the patella about the grinding surface, guiding the grinding surface to a predetermined medial portion of the patella, so that as the tool is moved, the patella is shaped to match an articulating surface of the femoral prosthesis.

The present invention further provides a method of profiling the anatomic patella, the method including the steps of connecting a guide member about the anatomic patella, guiding a grinding tool through the guide member and positioning a concave grinding surface of the tool against a posterior medial portion of the patella and grinding the medial portion into a hemispherical dome shape corresponding to the articulating surface of the patellar groove of the femoral component.

One advantage of the subject invention is that, during total knee arthroplasty, the anatomic patella can be profiled to positively track the femur component and thereby help to maintain positive ligament balance. Another advantage of the invention is that the interoperative patella profiling procedure is mechanically guided to grind the medial portion of the patella to precisely compliment to articulating surface of the femoral prosthesis. A still further advantage of the invention is that the patella profile in accordance with the invention will exhibit greater longevity as compared to patellas profiled according to the prior art techniques.

BRIEF DESCRIPTION OF THE FIGURES

Other advantages of the present invention will be readily appreciated as the same becomes better understood by reference to the following Detailed Description when considered in connection with the accompanying Drawings wherein:

FIG. 1 is an elevational view of the grinding tool made in accordance with the present invention;

FIG. 2 is a partial sectional view of FIG. 1, broken away to show an abrasive surface of the grinding tool; and FIG. 3 is an elevational view showing a pair of guide means clamped about an anatomic patella positioned adjacent the grinding tool of the present invention.

DETAILED DESCRIPTION

A system for profiling an anatomic patella is generally indicated at 10 in the FIGS. The system generally includes a grinding tool, generally shown at 12, and a grinding tool guide, generally shown at 13. The grinding tool 12 includes a handle portion 14 defining a longitudinal axis 16 of the tool. The handle 14 preferably includes an adapter 18 for attachment to a power device (not shown) for driving the rotation of the tool 12 about the axis 16. Alternatively, the handle 18 can be adapted for gripping manually by a practitioner to actuate the grinding operation.

The grinding tool 12 further includes an annular flanged portion 20 extending radially outwardly relative to the longitudinal axis 16. A neck portion 22 extends along the longitudinal axis 16 of the tool 12 from the flange portion 20 opposite the handle portion 14. The neck portion 22 includes an end grinding surface 24 which includes grinding teeth 26 for cutting or abraiding extending therefrom. The grinding surface 24 is a concave, hemispherical dome shape. The radius (curvature) which describes the dome shape complements the matching patella track formed in the femoral component (not shown) being implanted. In this manner, a surface is made on the patella conforming to the geometry of the prosthetic surface along which the patella tracks.

The flange portion 20 includes an abutment surface 28. The neck portion 22 is contiguous with and extends axially from the abutment surface 28.

The tool guide 13 includes a pair of patella clamp members 30,32. Member 30 is a substantially annular member including a substantially annular inner surface 34 having an end portion 36. Clamping means clamp the members 30,32 together so as to sandwich the patella therebetween and position the annular surface 34 about the medial portion of the patella so as to define a passageway having the medial portion of the patella positioned at its end. Member 32 can be of various shapes but preferably is a shape matching the shape of the other guide member 30.

The means for clamping members 30,32 together can take various forms. For example, the preferred means for clamping the member together is a state of the art patella clamp having a clamping end for engaging the patella on one side and receiving and guiding the grinding tool on the other side. It is critical that the clamping mechanism not interfere with the inner surface 34 of the clamping member 30.

In use, the guide members 30,32 are clamped about the anatomic patella 37 as shown in FIG. 3. The guide member 30 is positioned so as to expose the medial portion 38 of the inner aspect of the patella 37 within the passageway defined by the inner surface 34 of the member 30. The neck portion 22 of the grinding tool 12 is inserted in mating engagement with the inner surface 34 of the guide member 30 such that the guide member 30 guides the grinding tool 12 through the guide member 30 and positions the concave grinding surface 24 of the grinding tool 12 against the medial portion 38 of the anatomic patella 37. The surface of the patella 37 is then ground into a hemispherical dome shape to match the articulating (patellar track) surface of a femoral prosthetic component (not shown). Thusly, the intermedial aspect of the anatomic patella is made to positively track an implant, the dome surface causing positive tracking even where there is tilting between the patella and the femoral implant. This positive profiling of the anatomic patella should cause a decrease in pain to the patient while allowing soft tissue growth about the patella thus enhancing tracking along the patellar track surface of the femoral prosthetic component. An advantage of the subject resurfacing system and method is that positive function is maintained as well as ligament balance.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

What is claimed is:

1. A system for profiling an anatomic patella, the system comprising:
   (a) a tool including a handle portion and a neck portion having a first end operatively connected to the handle portion and having a second end terminating in a grinding surface for being pressed against a posterior surface of a patella, the grinding surface being shaped, sized and configured to complement an articulating surface of a femoral prosthesis and engage the posterior surface of the patella and defining a concave hemispherical domed shape for forming a hemispherical domed surface in the posterior surface of the patella, and
   (b) means for securing the patella as the grinding surface of the second end of the neck portion of the tool is pressed against the posterior surface of the patella and for guiding the grinding surface of the second end of the neck portion of the tool to a predetermined medial portion of the posterior surface of the patella so that as the second end of the neck portion of the tool is rotated, the predetermined medial portion of the posterior surface of the patella is shaped to match the articulating surface of the femoral prosthesis.

2. A system as set forth in claim 1 wherein the handle portion defines a longitudinal axis of the tool, the tool including an annular flange extending radially outwardly from one end of the handle portion, wherein the neck portion of the tool extends along the longitudinal axis from the flange portion opposite the handle portion, the flange portion defining an annular abutting surface about the neck portion, the means for securing and guiding includes a guide member having an inner surface defining a passageway for mating and guiding engagement with the second end of the neck portion and an end surface for abutting with the abutment surface to limit the amount that the neck portion can enter the passageway.

3. A system as set forth in claim 2 wherein the means for securing and guiding includes a pair of substantially annular guide members and connecting means for connecting the pair of guide members with a patella sandwiched therebetween, at least one of the guide members including the inner surface defining the passageway, the inner surface being annular, the neck portion of the tool being cylindrical for mating and guiding engagement with the inner surface.

4. A method of profiling an anatomic patella which comprises the step of grinding a hemispherical dome shape on a posterior surface of the patella using a tool including:
   (a) a handle portion; and
   (b) a neck portion having a first end operatively connected to the handle portion and having a second end terminating in a grinding surface for being pressed against and rotated about the posterior surface of the patella, the grinding surface defining a concave hemispherical domed shape for grinding a hemispherical dome shape on the posterior surface of the patella when pressed against and rotated relative to the posterior surface of the patella.

5. A method as set forth in claim 4 which comprises the additional step of securing the patella as the hemispherical dome shape is ground on the posterior surface thereof means including first and second clamp members to sandwich the patella therebetween, the first clamp member having an opening therethrough for positioning over the posterior surface of the patella and for guiding the second end of the neck portion of the tool to the posterior surface of the patella.

* * * * *